(12) United States Patent
Cheon et al.

(10) Patent No.: US 11,986,197 B2
(45) Date of Patent: May 21, 2024

(54) AUTONOMOUS ENDOSCOPIC SYSTEM AND CONTROL METHOD THEREFOR

(71) Applicants: ROEN Surgical, Inc., Daejeon (KR); KOREA ADVANCED INSTITUTE OF SCIENCE AND TECHNOLOGY, Daejeon (KR)

(72) Inventors: Byung Sik Cheon, Daejeon (KR); Dong Soo Kwon, Daejeon (KR); Deok Gyoon Chung, Daejeon (KR)

(73) Assignees: ROEN Surgical, Inc., Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 138 days.

(21) Appl. No.: 17/525,549

(22) Filed: Nov. 12, 2021

(65) Prior Publication Data

US 2022/0061868 A1  Mar. 3, 2022

Related U.S. Application Data

(63) Continuation of application No. 17/030,331, filed on Sep. 23, 2020, now Pat. No. 11,172,950, which is a
(Continued)

(30) Foreign Application Priority Data

Apr. 12, 2018 (KR) .................. 10-2018-0042794
Apr. 12, 2019 (KR) .................. 10-2019-0043033

(51) Int. Cl.
*A61B 17/221* (2006.01)
*A61B 1/00* (2006.01)
(Continued)

(52) U.S. Cl.
CPC ........ *A61B 17/221* (2013.01); *A61B 1/00045* (2013.01); *A61B 1/00085* (2013.01);
(Continued)

(58) Field of Classification Search
CPC ............ A61B 1/00045; A61B 1/00085; A61B 1/00142; A61B 1/00147; A61B 1/0052; A61B 1/00154; A61B 1/0016
See application file for complete search history.

(56) References Cited

U.S. PATENT DOCUMENTS

| 5,876,325 A | 3/1999 | Mizuno et al. |
| 2002/0022765 A1 | 2/2002 | Belson |

(Continued)

FOREIGN PATENT DOCUMENTS

| KR | 20170107618 A | 9/2017 |
| KR | 2018-0004001 A | 1/2018 |

OTHER PUBLICATIONS

Alfred M. Franz et al., "Electromagnetic Tracking in Medicine—A Review of Technology, Validation, and Applications," IEEE Transactions on Medical Imaging, vol. 33, Aug. 2014, pp. 1702-1725.

*Primary Examiner* — Aaron B Fairchild
(74) *Attorney, Agent, or Firm* — JCIPRNET

(57) ABSTRACT

An autonomous endoscopic system capable of controlling movement of an endoscope inserted into a protective sheath installed in the body of a patient includes: an endoscope operating device capable of operating a relative position of the endoscope with respect to the protective sheath, a rolling angle of the endoscope, and a bending angle of a bending portion which is located at the end of the endoscope and is bendable; and a control unit for controlling the endoscope operating device, wherein the control unit controls the endoscope operating device on the basis of a driving record of the endoscope.

13 Claims, 13 Drawing Sheets

Related U.S. Application Data continuation of application No. PCT/KR2019/004453, filed on Apr. 12, 2019.

(51) Int. Cl.
*A61B 1/005* (2006.01)
*A61B 1/307* (2006.01)
*A61B 90/00* (2016.01)
*A61B 17/00* (2006.01)
*A61B 17/22* (2006.01)

(52) U.S. Cl.
CPC ...... *A61B 1/00108* (2013.01); *A61B 1/00142* (2013.01); *A61B 1/00147* (2013.01); *A61B 1/00154* (2013.01); *A61B 1/0052* (2013.01); *A61B 1/307* (2013.01); *A61B 90/06* (2016.02); *A61B 90/36* (2016.02); *A61B 2017/00212* (2013.01); *A61B 2017/0034* (2013.01); *A61B 2017/22038* (2013.01); *A61B 2017/22084* (2013.01); *A61B 2017/2215* (2013.01); *A61B 2090/061* (2016.02)

(56) References Cited

U.S. PATENT DOCUMENTS

| | | |
|---|---|---|
| 2007/0173093 A1 | 7/2007 | Kura et al. |
| 2008/0058836 A1* | 3/2008 | Moll ............... A61B 34/32 606/130 |
| 2009/0287043 A1 | 11/2009 | Naito et al. |
| 2010/0022825 A1 | 1/2010 | Yoshie |
| 2011/0208000 A1 | 8/2011 | Honda et al. |
| 2012/0289777 A1 | 11/2012 | Chopra et al. |
| 2012/0294498 A1* | 11/2012 | Popovic ............ A61B 1/0005 382/128 |
| 2015/0230689 A1 | 8/2015 | Blohm et al. |
| 2015/0257847 A1 | 9/2015 | Higgins et al. |
| 2016/0007836 A1 | 1/2016 | Kikuchi |
| 2016/0324399 A1 | 11/2016 | Banju et al. |
| 2016/0360120 A1 | 12/2016 | Inoue |
| 2017/0119412 A1 | 5/2017 | Noonan et al. |

\* cited by examiner

AUTONOMOUS ENDOSCOPIC SYSTEM AND CONTROL METHOD THEREFOR

CROSS-REFERENCE TO RELATED APPLICATIONS

This application is a continuation application of U.S. patent application Ser. No. 17/030,331 filed on Sep. 23, 2020, which is a continuation of PCT international application No. PCT/KR2019/004453 filed on Apr. 12, 2019, and claims priority to Korean patent Application No. 10-2018-0042794 filed on Apr. 12, 2018, and Korean patent Application No. 10-2019-0043033 filed on Apr. 12, 2019, the entire disclosures of which are hereby incorporated by reference.

TECHNICAL FIELD

Embodiments relate to an autonomous endoscopic system and control method therefor.

BACKGROUND ART

An endoscope is a medical instrument used to directly investigate internal organs or the inside of body cavities. The endoscope is designed to be inserted into the body to observe an organ with a lesion that cannot be directly seen without performing surgery or autopsy. There are many types of endoscopes such as, for example, a bronchoscope, an esophagoscope, a gastroscope, a duodenoscope, a proctoscope, a cystoscope, a laparoscope, and a ureteroscope.

For example, endoscopic surgery using a ureteroscope is known as the most frequently used, reliable method to remove kidney stones. In detail, the method is performed in the manner of inserting the ureteroscope through the ureter to reach a kidney using radiodiagnostic equipment such as C-arm, fragmenting stones with a laser, and extracting the stones using a basket. Here, the laser and the basket are inserted through a channel inside the ureteroscope.

Meanwhile, the radiodiagnostic equipment should be continuously used to check the position of the endoscope in the body. Thus, doctors and patients are at risk of radiation exposure. In particular, surgery is highly difficult since a very slender endoscope like a ureteroscope has a limited degree of freedom (bending 1 DOF), and there may be communication issues between two operators who need to perform precise works together. In addition, the surgery precision may decrease when the arms of an operator are fatigued over time as the operator should hold the endoscope for a long time. As described above, the endoscopic surgery requires precision, which results in the high fatigue of the operator. In addition, since it is impossible to accurately measure the size of stone using the endoscope alone, there may occur a medical accident such as hurting the ureter of a patient in the process of withdrawing a stone that is not fragmented sufficiently. If the ureter is damaged, surgery is immediately performed through an incision, and after that, there may be fatal aftereffects.

In consideration of such issues, there is a need for endoscopic equipment that may reduce the risk of radiation exposure of doctors and patients, reduce fatigue, and prevent medical accidents.

The above description has been possessed or acquired by the inventor(s) in the course of conceiving the present invention and is not necessarily an art publicly known before the present application is filed.

DISCLOSURE OF INVENTION

Technical Goals

An aspect provides an autonomous endoscopic system and control method therefor.

Technical Solutions

According to an aspect, there is provided an autonomous endoscopic system capable of controlling movement of an endoscope inserted into a protective sheath installed in the body of a patient, the autonomous endoscopic system including an endoscope operating device capable of adjusting a relative position of the endoscope with respect to the protective sheath, a rolling angle of the endoscope, and a bending angle of a bending portion which is located at the end of the endoscope and is bendable, and a control unit for controlling the endoscope operating device, wherein the control unit may control the endoscope operating device on the basis of a driving record of the endoscope.

The autonomous endoscopic system may further include a sensor for sensing information about the relative position of the endoscope with respect to the protective sheath, wherein the driving record may include information about a relative movement of the endoscope with respect to the protective sheath.

The sensor may include a first magnetic body and a second magnetic body installed on the protective sheath and the endoscope, respectively.

A basket for gripping a stone present inside the body of the patient may be inserted into the endoscope, and the control unit may control the endoscope operating device such that the endoscope automatically returns to the site where the endoscope was located at a point in time the basket completes a gripping operation.

A basket for gripping a stone present inside the body of the patient may be inserted into the endoscope, and when the basket completes a gripping operation, the control unit may control the endoscope operating device (a) to withdraw the endoscope from the protective sheath, (b) to release the gripped stone by opening the basket, and (c) to cause the endoscope to re-enter, such that the endoscope automatically returns to the site where the endoscope was located at a point in time the basket completes the gripping operation.

The driving record may include an operation profile that shows an operation amount of the endoscope operating device over time from a first point in time to a second point in time.

The first point in time may be a point in time the end of the endoscope is located at a particular site with respect to the protective sheath.

The second point in time may be a point in time at which a surgical instrument inserted into the endoscope performs a particular work.

At least one of the first point in time and the second point in time may be an optional point in time to be set by an operator.

The operation amount may include a translation amount of the endoscope, a rolling angle variation of the endoscope, and a bending angle variation of the endoscope.

The control unit may (a) determine whether there is, between the first point in time and the second point in time, a forward-backward movement interval during which the endoscope passes a particular position and then returns again, (b) generate, if there is a forward-backward movement interval, a shortened profile by removing an operation amount over time during the forward-backward movement interval from the operation profile, and (c) control the endoscope operating device according to the shortened profile.

The control unit may (a) determine whether there is, between the first point in time and the second point in time, a forward-backward movement interval during which the endoscope passes a particular position and then returns again, (b) generate, if there is a forward-backward movement interval, a corrected profile that includes a rolling angle variation and a bending angle variation during the forward-backward movement interval, that does not include a translation amount during the forward-backward movement interval, and that is performed for a time shorter than the forward-backward movement interval, (c) generate a shortened profile by replacing an operation amount over time during the forward-backward movement interval in the operation profile with the corrected profile, and (d) control the endoscope operating device according to the shortened profile.

The control unit may initialize a pose of the endoscope such that the endoscope has a particular rolling angle and a particular bending angle when the end of the endoscope is located at a particular site with respect to the protective sheath.

The autonomous endoscopic system may further include a display for outputting an image of the inside of the body of the patient to an operator, wherein the control unit may display the image by overlaying, on the image, an expected position and pose of the endoscope at a point in time after a set time elapses from a current time.

The autonomous endoscopic system may further include a clutch operable by an operator and capable of allowing or stopping a continuous drive of the endoscope operating device.

The autonomous endoscopic system may further include a master device located at a site spaced apart from the endoscope operating device and operated by an operator to remotely operate the endoscope operating device.

Effects

According to embodiments, an endoscope may autonomously drive to a particular position based on kinematic driving records, and thus it is possible to remarkably reduce the surgery fatigue of an operator.

According to embodiments, particularly in the case of kidney stone surgery, it is possible to automatically perform repeated works such as repeatedly inserting and withdrawing an endoscope to withdraw a number of stone fragments at a particular site one by one.

According to embodiments, particularly in the case of kidney stone surgery, it is possible to quickly perform work such as repeatedly accessing a particular position, which is very difficult due to the complex internal structure, based on previous driving records. Further, it is possible to access the particular position along the shortest path based on the previous driving records, and thus the operation time may be considerably reduced. Consequently, the time for general anesthesia of a patient may be reduced, which may improve the stability of surgery, in particular, for elderly patients. According to the simulation results, the operation time of 2 hours on average may be reduced to 1 hour or less.

BEST MODE FOR CARRYING OUT THE INVENTION

Figure 1:
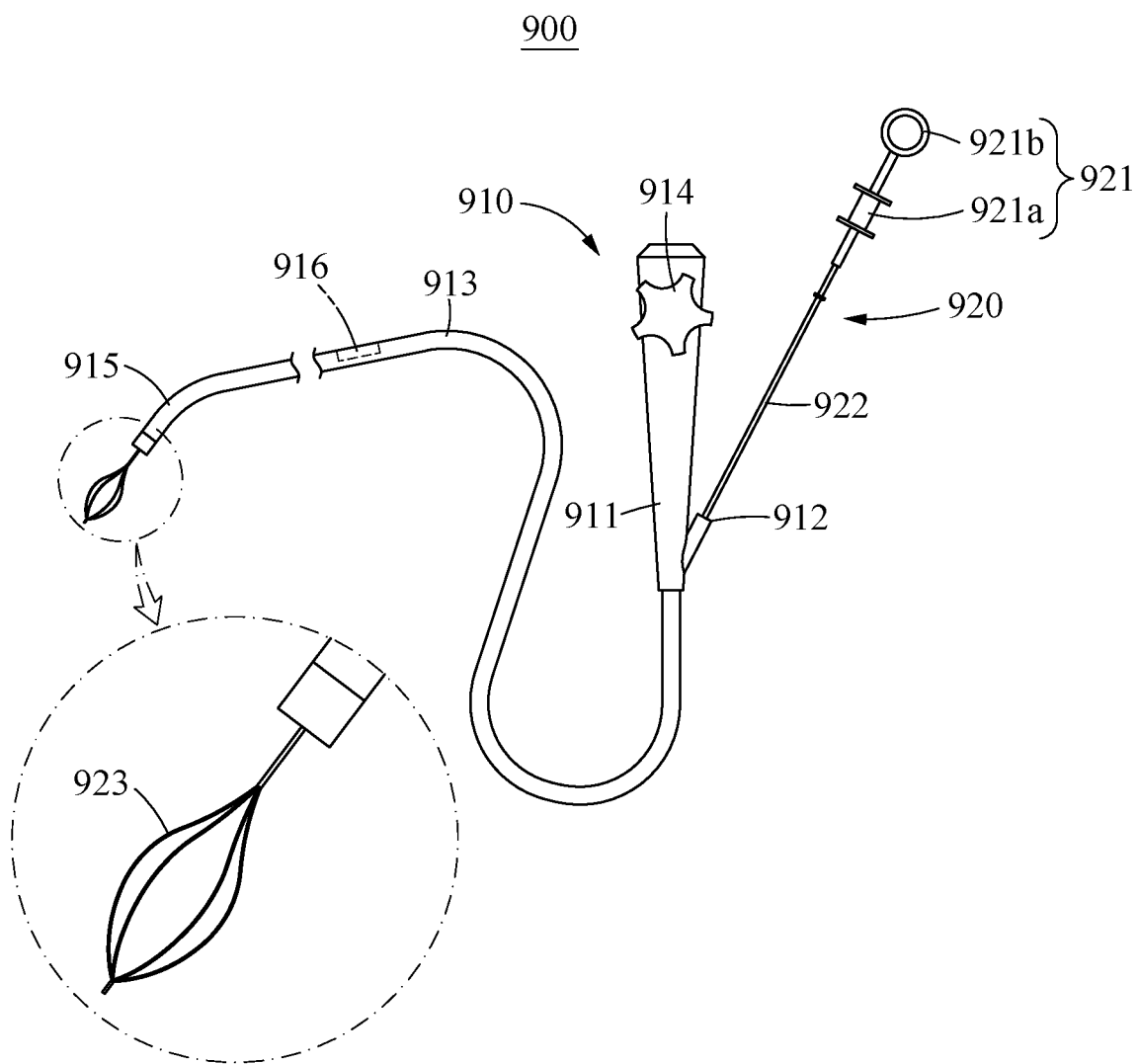
FIG. 1 illustrates an apparatus for endoscopic surgery according to an embodiment.

Hereinafter, embodiments of the present disclosure will be described with reference to the accompanying drawings. Regarding the reference numerals assigned to the components in the drawings, it should be noted that the same components will be designated by the same reference numerals, wherever possible, even though they are shown in different drawings. Also, in the description of the embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the embodiments described above and an element having a common function. Unless otherwise mentioned, the descriptions on the embodiments may be applicable to the following embodiments and thus, duplicated descriptions will be omitted for conciseness.

FIG. 1 illustrates an apparatus for endoscopic surgery according to an embodiment.

Referring to FIG. 1, an apparatus for endoscopic surgery 900 may include an endoscope 910 and a surgical instrument 920.

The endoscope 910 may include a control handle 911 to be gripped by an operator with a hand, an instrument hole 912 configured to guide the surgical instrument 920, an insertion tube 913 connected to the control handle 911 and to be inserted into the body, a bending portion 915 located at the end of the insertion tube 913 and configured to perform a bendable motion, a knob 914 provided rotatably in the control handle 911 and configured to adjust an angle of the bending portion 915 according to manipulation, and a magnetic body 916 provided in the insertion tube 913. The function of the magnetic body 916 will be described later.

The surgical instrument 920 may include an operation part 921 to be gripped with a hand and operated by the operator, a surgical instrument cable 922 connected to the operation part 921 and to be inserted into the insertion tube 913 of the endoscope 910, and an action part 923 provided at the end of the surgical instrument cable 922 and to be operated by the operation part 921. The action part 923 may include, for example, a basket capable of gripping a stone present inside the body of a patient. Hereinafter, a case where the action part 923 is a basket will be described as an example. However, differently, the action part 923 may be another means known to those skilled in the art, such as a laser lithotripter that fragments stones.

For example, the operation part 921 may include a first operation unit 921b and a second operation unit 921b, wherein the operation part 921 may operate the action part of the surgical instrument 920 by moving the second operation unit 921b, which moves relatively with respect to the first operation unit 921b, toward the first operation unit 921b. According to the operation of the operation part 921, the action part 923 may perform a particular work (for example, operating the basket or operating the laser lithotripter).

Figure 2:
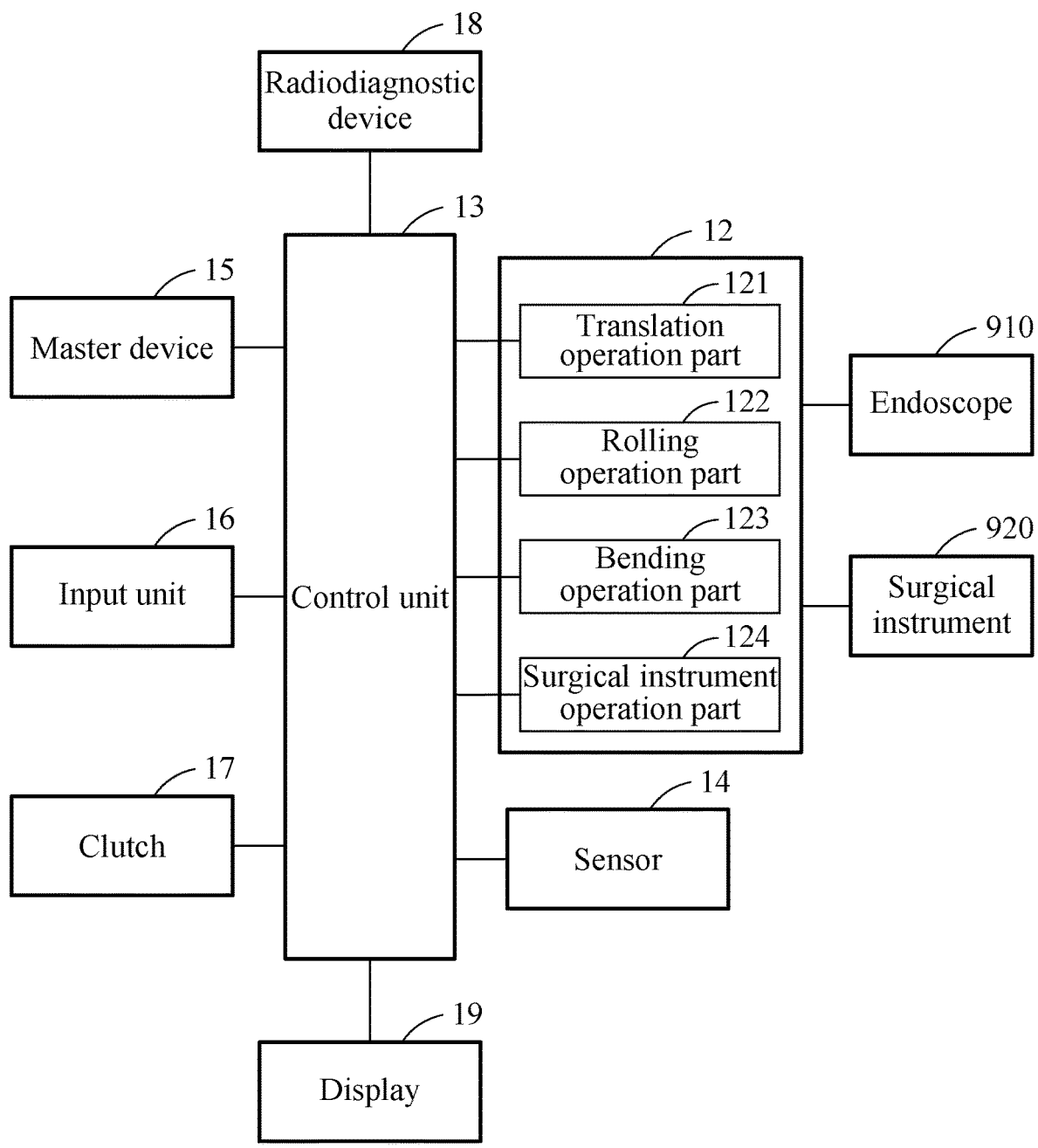
FIG. 2 is a block diagram illustrating an autonomous endoscopic system according to an embodiment.
Figure 3:
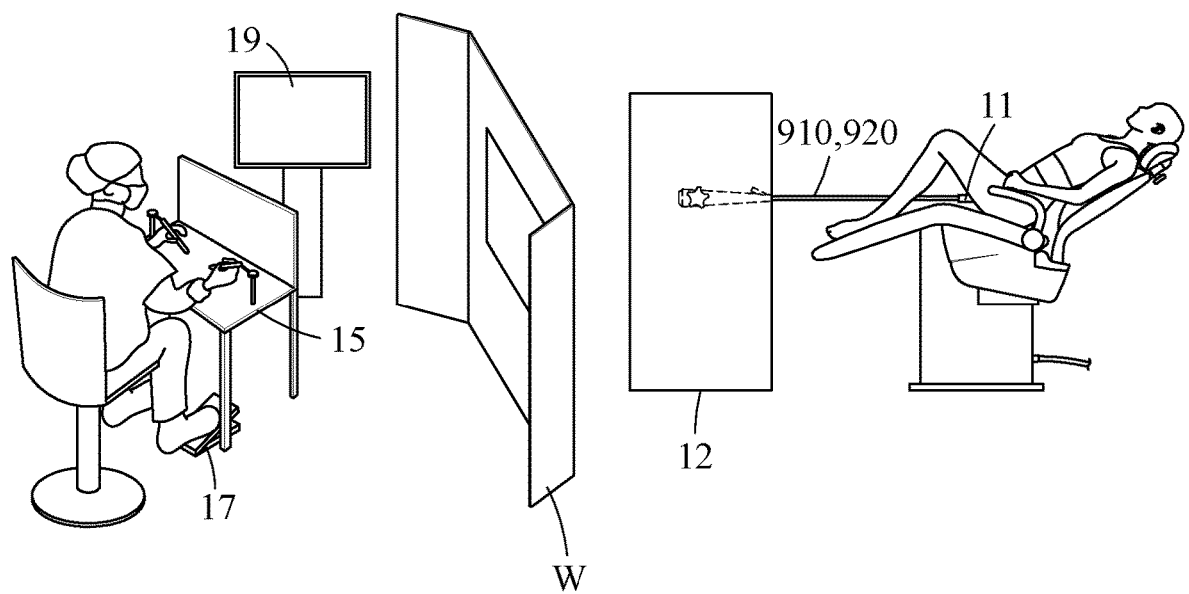
FIG. 3 illustrates a configuration of an autonomous endoscopic system according to an embodiment.

FIG. 2 is a block diagram illustrating an autonomous endoscopic system according to an embodiment, and FIG. 3 illustrates a configuration of an autonomous endoscopic system according to an embodiment.

Referring to FIGS. 2 and 3, an autonomous endoscopic system 1 may control a movement of the endoscope 910 inserted into a protective sheath 11 or a movement of the surgical instrument 920 inserted through the endoscope 910. For example, the autonomous endoscopic system 1 may include an endoscope operating device 12, a control unit 13, a sensor 14, a master device 15, an input unit 16, a clutch 17, a radiodiagnostic device 18, a display 19, and a radiation shield wall W.

The protective sheath 11 may be placed in the body of the patient to prevent damage to the body of the patient by friction with the endoscope 910. The protective sheath 11 includes a protective hole provided in a length direction thereof to guide the endoscope 910.

The endoscope operating device 12 may provide a driving force to drive, roll or bend the endoscope 910, or provide a driving force for the surgical instrument 920 to perform a particular work. For example, the endoscope operating device 12 may have a structure that is attachable to and detachable from a commercial endoscope and/or a commercial surgical instrument. The endoscope operating device 12 may have a structure that is physically fastenable to each operation part of the commercial endoscope and/or the commercial surgical instrument, and may operate the commercial endoscope and/or the commercial surgical instrument based on a signal input through the master device 15 by driving the fastened part. Meanwhile, instead of using a commercial endoscope and/or a commercial surgical instrument, an endoscope and/or surgical instrument dedicated to the endoscope operating device 12 may be used, and the endoscope operating device 12 may be formed integrally with the endoscope and/or surgical instrument. The endoscope operating device 12 may include a translation operation part 121, a rolling operation part 122, a bending operation part 123, and a surgical instrument operation part 124.

The translation operation part 121 may adjust a relative position of the endoscope 910 with respect to the protective sheath 11. For example, the translation operation part 121 may include a driving source configured to move the entire endoscope 910 forward or backward by moving, along a linear guide rail, a block with the control handle 911 of the endoscope 910 mounted.

The rolling operation part 122 may manipulate a rolling angle of the endoscope 910. For example, the rolling operation part 122 may include a driving source configured to rotate, based on an axial direction of the endoscope 910, the block with the control handle 911 of the endoscope 910 mounted.

The bending operation part 123 may adjust a bending angle of the bending portion 915 of the endoscope 910. For example, the bending operation part 123 may include a driving source configured to pull a wire inserted into the bending portion 915.

The surgical instrument operation part 124 may include, on the block with the control handle 911 of the endoscope 910 mounted, a drive source configured to relatively move with respect to the block and drive another block with the surgical instrument 920 mounted.

Meanwhile, the above description is only an example of the endoscope operating device 12. As another example, unless otherwise mentioned, any slave device operable with a master-slave relationship may be used as the endoscope operating device 12, for example, as in KR 1882093, JP 2010-279688, and JP 2007-117394.

The control unit 13 may control the endoscope operating device 12. The control unit 13 may operate the endoscope 910 and the surgical instrument 920 by controlling the endoscope operating device 12 based on control signals input through the sensor 14, the master device 15, the input unit 16, and/or the clutch 17. The control unit 13 may enable the endoscope 910 to autonomously drive by controlling the endoscope operating device 12 based on a driving record of the endoscope 910, which will be described later with reference to FIG. 6, and the like. The driving record may include, for example, information about relative movements (translation, rolling, and bending) of the endoscope 910 with respect to the protective sheath 11.

The sensor 14 may sense information about the relative position of the endoscope 910 with respect to the protective sheath 11. The control unit 13 may control the endoscope operating device 12 based on the information sensed by the sensor 14.

For example, the sensor 14 may include a first magnetic body 111 (see FIG. 4) and a second magnetic body 916 (see FIG. 1) provided on the protective sheath 11 and the endoscope 910, respectively. For example, the first magnetic body 111 may be provided at a particular site on the protective sheath 11, and the second magnetic body 916 may be provided at a particular site on the insertion tube 913. The control unit 13 may sense the relative position of the endoscope 910 with respect to the protective sheath 11 based on a magnitude of magnetic force acting between the first magnetic body 111 and the second magnetic body 916. For example, the first magnetic body 111 may be provided at a position biased to one side with respect to a longitudinal center line of the protective sheath 11. Likewise, the second magnetic body 916 may be provided at a position biased to one side with respect to a longitudinal center line of the insertion tube 913. By the structure described above, the control unit 13 may sense a relative rolling angle of the endoscope 910 with respect to the protective sheath 11.

As another example, the sensor 14 may be a displacement sensor connected between the protective sheath 11 and the endoscope 910 to sense a change in relative position.

As still another example, the sensor 14 may sense a translation amount, a rolling angle, a bending angle, and/or an operation of the endoscope 910 (for example, whether an operation of gripping a basket is performed), by sensing the operation amount of the endoscope operating device 12.

In the present application, the sensor 14 may include any means capable of sensing the information about the relative position of the endoscope 910 with respect to the protective sheath 11, in addition to the means exemplarily proposed above. For example, the radiodiagnostic device 18 may function as the sensor 14, which will be described later.

The master device 15 may be located at a site spaced apart from the endoscope operating device 12 and operated by an operator to remotely operate the endoscope operating device 12. The master device 15 shown in FIG. 3 is only an example, and the type of the master device 15 is not limited in the scope of the present invention.

The input unit 16 may receive an instruction from an operator and transmit the instruction to the control unit 13. For example, the input unit 16 may include a known user interface, such as a keyboard or a mouse. The operator may select an interval to store the driving record of the endoscope 910 through the input unit 16.

The clutch 17 may be operable by the operator, and receive the instruction from the operator and transmit the instruction to the control unit 13, thereby allowing or stopping a continuous drive of the endoscope operating device 12. For example, the clutch 17 may have a foot pedal structure which allows input of information through a foot, rather than using a hand of a user, as shown in FIG. 3.

The radiodiagnostic device 18 may capture and image the inside of the body of the patient. The radiodiagnostic device 18 may provide the operator with the position of the endoscope 910. For example, a C-arm may be utilized as the radiodiagnostic device 18.

By the radiodiagnostic device 18, the position of the protective sheath 11 may be easily known. Further, the protective sheath 11 may maintain a fixed position inside the body of the patient irrespective of the movement of the endoscope 910, and the protective sheath 11 and the endoscope operating device 12 may remain fixed to each other through a fixing tool. By the structure described above, it is possible to collect the relative position between the protective sheath 11 and the endoscope 910 through image processing from an image obtained through the radiodiagnostic device 18, and drive the endoscope 910 based on the collected information. In other words, when the radiodiagnostic device 18 is used, it is possible to operate the endoscope 910 even without using the magnetic bodies 111 and 916 as described above. In detail, the control unit 13 may sense the relative position of the endoscope 910 with respect to the protective sheath 11 based on the image obtained using the radiodiagnostic device 18. In this regard, the radiodiagnostic device 18 may be construed as being included in the sensor 14.

The display 19 may provide the operator with the image of the inside of the body of the patient through a camera mounted on the radiodiagnostic device 18 and/or the endoscope 910. For example, the operator may select, on the display 19 by a screen touch or mouse click, the end of the protective sheath 11 and the position of a particular part (for example, a minor calyx) of the organs of the patient, and the control unit 13 may extract a relative distance between the two selected points and provide the operator with the extracted relative distance.

For example, in an autonomous driving mode, the control unit 13 may determine an expected position and pose of the endoscope 910 at a point in time after a set time elapses from a current time, and display the expected position and pose through the display 19 by overlaying a semitransparent image of the expected position and pose, on the image of the inside of the body of the patient. In this state, the operator may operate the clutch 17 to determine whether to continue allowing the autonomous driving of the endoscope 910 without an additional operation, or stop or end the autonomous driving as necessary and directly drive the endoscope 910 using the master device 15. By the configuration described above, when an error occurs due to aging and a degree of bending angle of the endoscope 910, the operator may correct the error by intervening in the adjustment, whereby the stability of surgery may improve significantly. Further, the control unit 13 may collect the information corrected by the operator intervening in the adjustment and use the collected information as big data of a deep learning algorithm to reduce driving errors of the endoscope 910.

The radiation shield wall W may be provided between an area where the operator is located and an area where the patient is located. In other words, the radiation shield wall W may be provided between the master device 15 and the endoscope operating device 12 to separate two areas, that is, the area where the operator is located and the area where the patient is located. By the radiation shield wall (W) described above, it is possible to reduce the risk of radiation exposure by the radiodiagnostic device 18 affecting the operator who performs surgery on a large number of patients.

Figure 4:
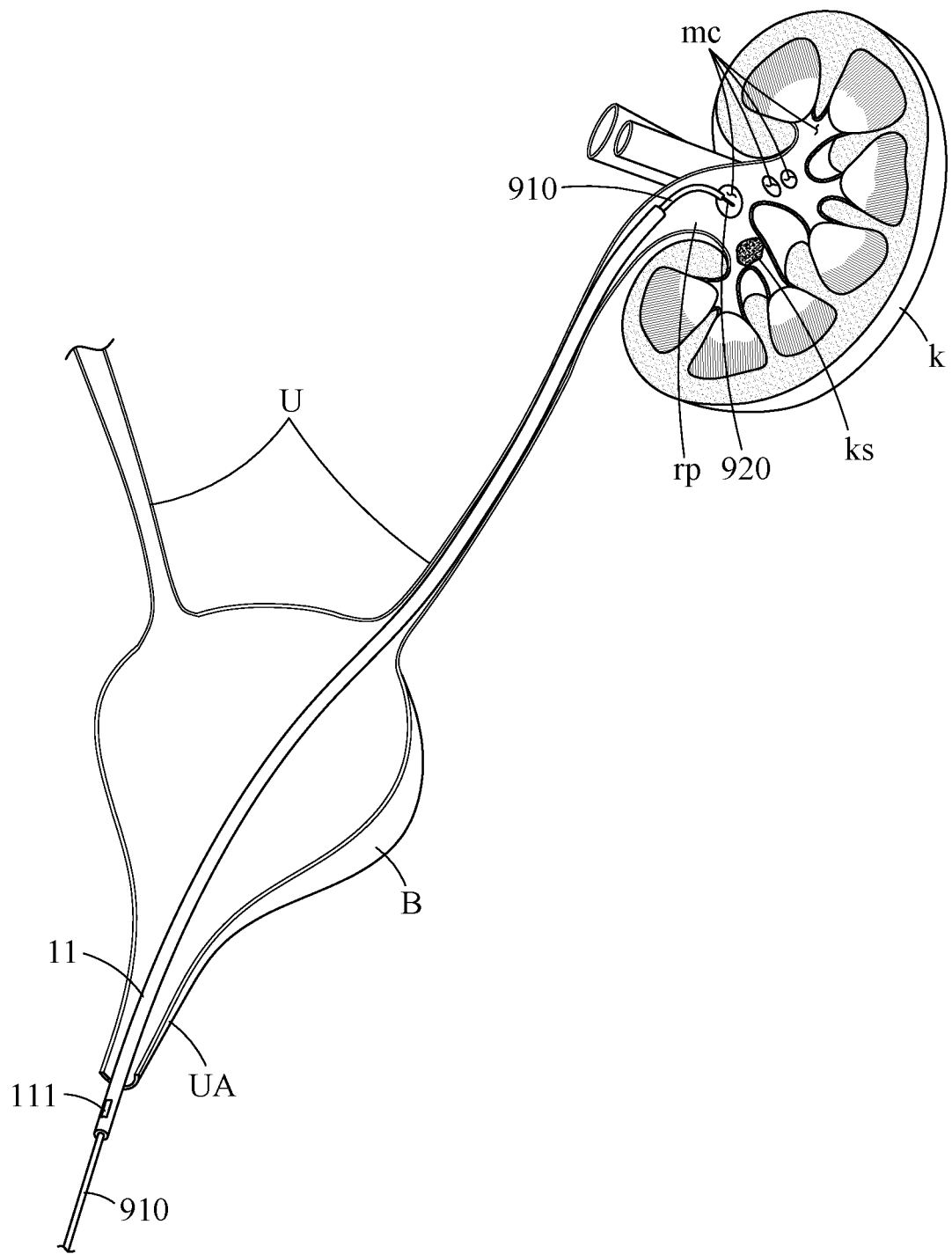
FIG. 4 illustrates an endoscope inserted into the body of a patient.
Figure 5:
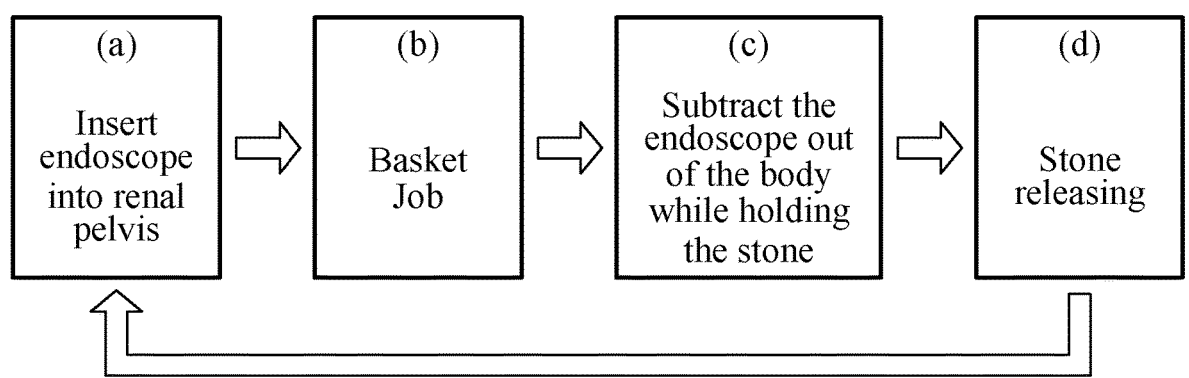
FIG. 5 illustrates a general procedure of kidney stone removal surgery.

FIG. 4 illustrates an endoscope inserted into the body of a patient, and FIG. 5 illustrates a general procedure of kidney stone removal surgery.

Referring to FIGS. 4 and 5, a procedure of kidney stone removal surgery performed using a ureteroscope is shown. Kidney stones (ks) are mostly located in a minor calyx (mc) of the kidney (k). For kidney stone removal surgery, the protective sheath 11 is inserted through the urethra (UA) of the patient, passes through the bladder (B) and the ureter (U), and is placed such that the end of the protective sheath 11 is located at the renal pelvis (rp), the part connected to the ureter (U) of the kidney k. In this state, the endoscope 910 is inserted along the protective sheath 11, and the operator may scan for a kidney stone (ks) by operating the endoscope 910 in a state in which the bending portion of the endoscope 910 passes through the end of the protective sheath 11 to be located in the vicinity of the renal pelvis (rp). Meanwhile, although FIG. 4 simply illustrates the internal structure of the kidney (k), the kidney (k) has a much more complex internal structure in reality. In addition, there is a problem in that the radioactivity of the radiodiagnostic device 18 needs to be continuously used to obtain an image of the movement of the endoscope 910 viewed from the third-person point of view. Therefore, a work of finding a kidney stone (ks) is performed through the camera of the endoscope 910 mainly at the first-person point of view. However, it is impossible to know the rolling angle and the bending angle from the image viewed through the endoscope 910 without using other external information, and thus, it is difficult to determine the directivity. Particularly, a minor calyx (mc) where a kidney stone (ks) is mostly found has a multi-branch structure, and thus, it is not easy to determine a minor calyx (mc) to enter.

Further, once a kidney stone (ks) is found, a process of fragmenting the kidney stone and repeatedly withdrawing a number of fragments of the stone from the body of the patient using the basket 923 (see FIG. 1), together with the endoscope, is required. For example, when a stone with a diameter of 1 cm is deconstructed into pieces with a diameter of 2 mm, a total of 125 repetitive insertion and withdrawal works are required. In other words, the process shown in FIG. 5 should be repeated 125 times per 1 stone (ks).

In the state in which the stone is fragmented, the endoscope 910 needs to move tens of times along the same path to the same minor calyx (mc) to withdraw the stone fragments, and thus, the fatigue of the operator is continuously accumulated. In addition, if the operator places, in reality, the endoscope 910 in another minor calyx (mc), rather than placing the endoscope 910 at the previous work position in the same minor calyx (mc), the operation time may increase, or the surgery may not be performed perfectly.

Meanwhile, since the kidney (k) is a relatively solid organ compared with the other organs, the kidney (k) is generally maintained in the same position during the surgery. Consequently, except the basket job (b) of the procedure shown in FIG. 5, at least one of a total of three remaining operations: (a) inserting the end of the endoscope 910 to be located at the renal pelvis (rp); (c) withdrawing the endoscope 910 from the body of the patient and the protective sheath 11 while holding a stone; and (d) releasing the stone from the withdrawn endoscope 910 by opening the basket, may be performed automatically, which will be described with reference to FIG. 6, and the like. In doing so, it is possible to reduce the fatigue of the operator and to perform stone removal surgery faster and more accurately.

Figure 6:
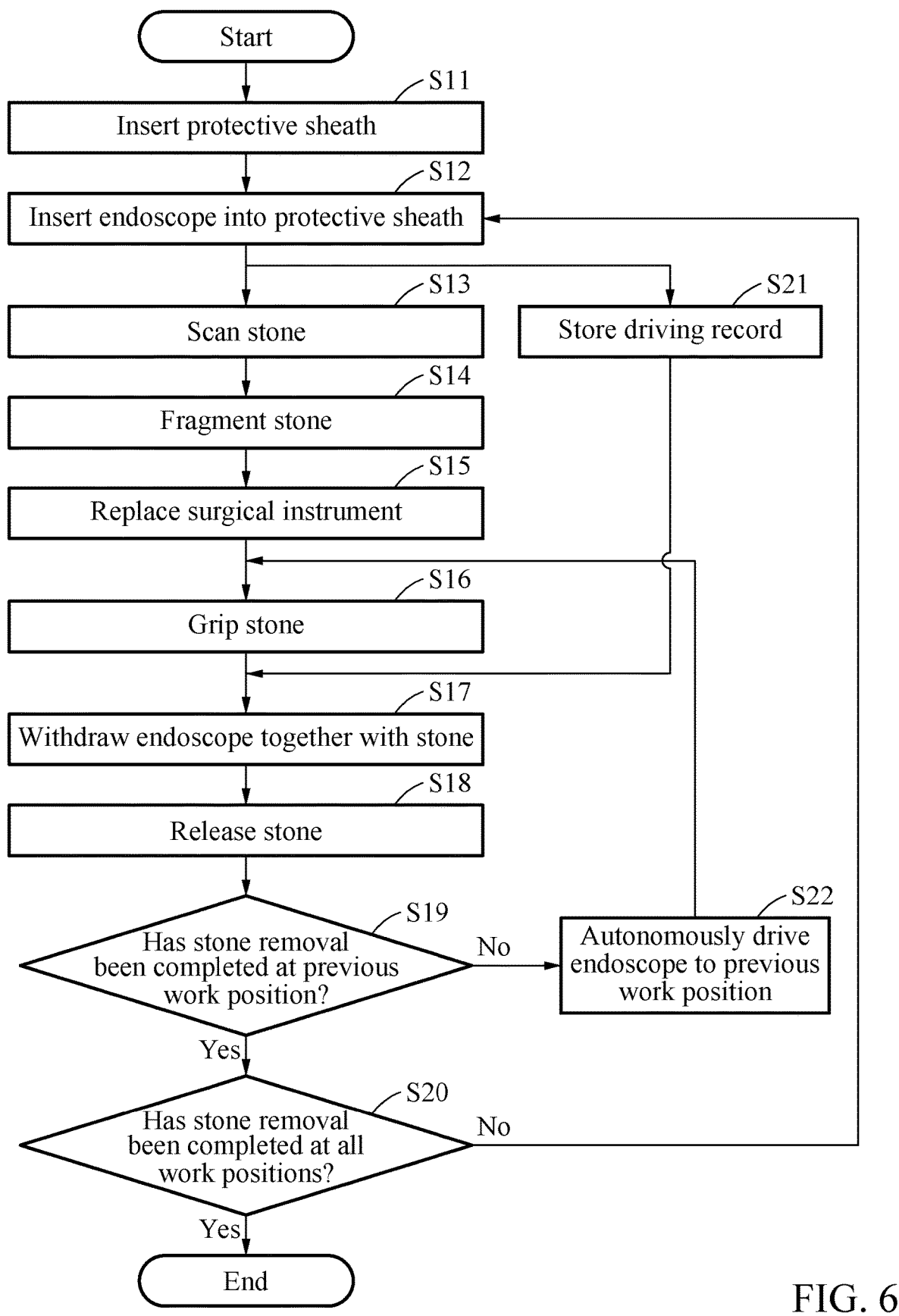
FIG. 6 is a flowchart illustrating a control method for an autonomous endoscopic system according to an embodiment.
Figure 7:
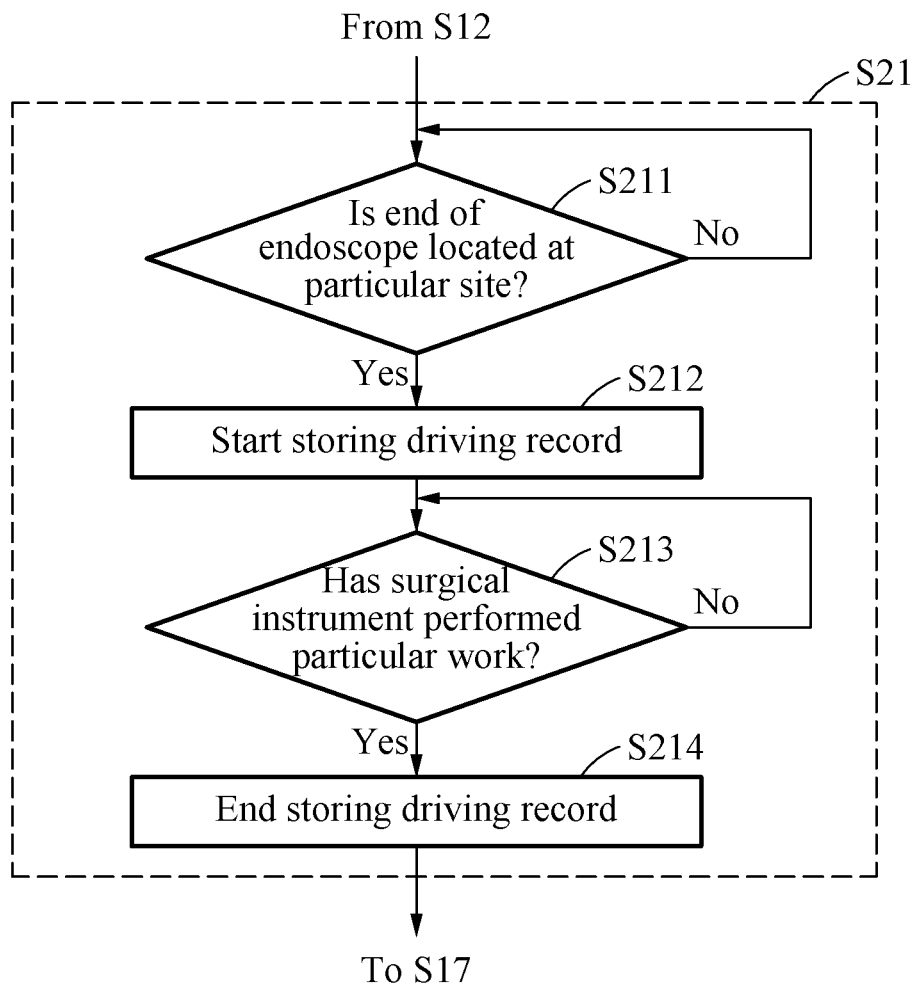
FIGS. 7 and 8 illustrate an operation of storing a driving record according to an embodiment.
Figure 8:
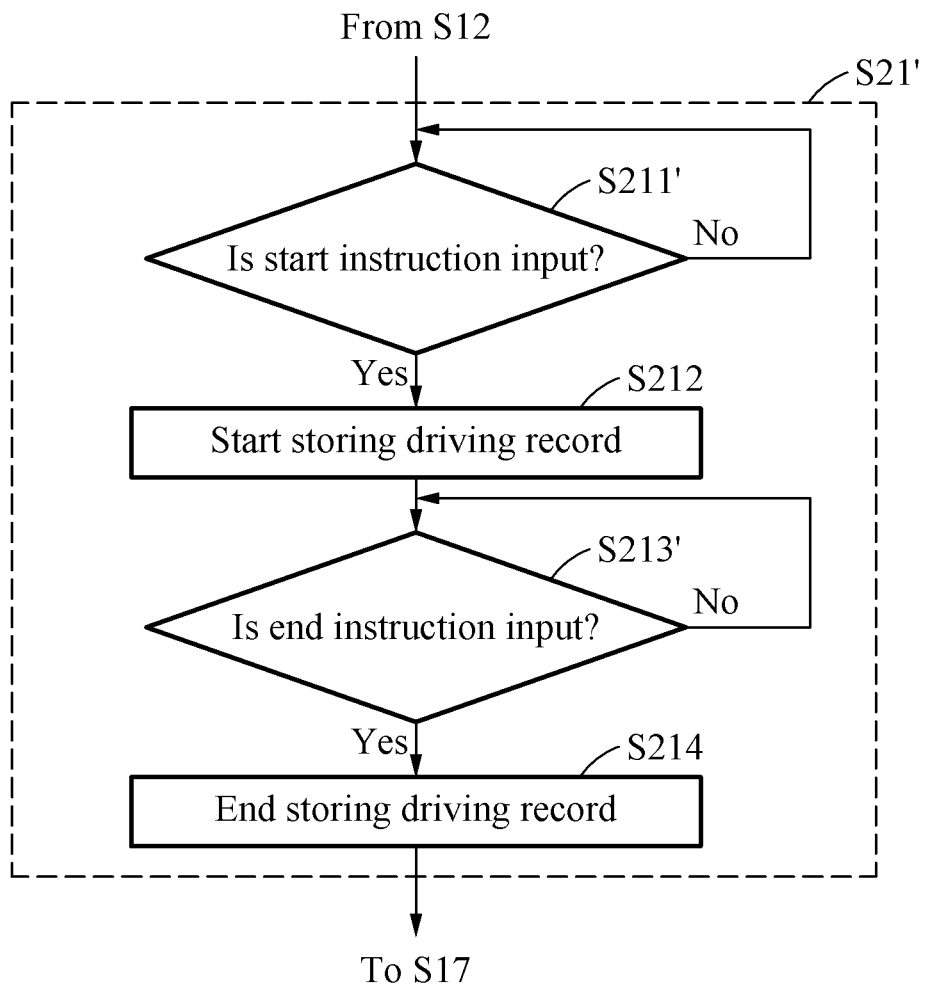

FIG. 6 is a flowchart illustrating a control method for an autonomous endoscopic system according to an embodiment, and FIGS. 7 and 8 illustrate an operation of storing a driving record according to an embodiment.

Referring to FIGS. 6 to 8, a control method for the autonomous endoscopic system 1 may be performed as follows. Hereinafter, kidney stone removal surgery will be exemplarily described. However, unless otherwise described, it is obvious to those skilled in the art that the embodiment may also be applicable to other surgery.

First, in operation S11, the operator may insert the protective sheath 11 into the body of the patient. The protective sheath 11 may be inserted to pass through the urethra, the bladder, and the ureter of the patient such that the end thereof is located in the renal pelvis of the kidney.

In operation S12, the endoscope operating device 12 may translate the endoscope 910 along the inside of the protective sheath 11. Meanwhile, through information sensed by the sensor 14 during the translation movement of the endoscope 910, the control unit 13 may control the endoscope operating device 12 such that the end of the endoscope 910 is located at a particular site with respect to the protective sheath 11 and/or at a particular rolling angle. This process may be performed regardless of the driving record of the endoscope 910. Operation S12 may also be referred to as an initialization operation. For example, the control unit 13 may initialize the pose of the endoscope 910 such that the endoscope 910 has a particular rolling angle and a particular bending angle when the end of the endoscope 910 is located at a particular site with respect to the protective sheath 11. The particular site may be the renal pelvis from which it is easy for the end of the endoscope 910 to access most of the minor calyces.

In operation S13, the operator may scan for a stone by operating the endoscope 910 using the master device 15. If a stone is found, the operator may fragment the stone by operating the surgical instrument 920 using the master device 15, in operation S14. Thereafter, in operation S15, while the endoscope 910 is maintained at the same position and pose, the operator may replace the surgical instrument 920 such as a stone fragmenting tool (for example, a laser lithotripter) with a stone gripping tool (for example, a basket). In operation S16, the operator may perform the basket job of gripping the stone.

While the operator operates the master device 15, the driving record of the endoscope 910 from a first point in time to a second point in time may be stored, in operation S21. In operation S21, an operation amount of the endoscope 910 operated by the endoscope operating device 12 may be recorded over time. Such an operation amount over time may be referred to as an "operation profile". Meanwhile, the "operation amount" may include a translation amount of the endoscope 910, a rolling angle variation of the endoscope 910, and a bending angle variation of the endoscope 910. Examples of the operation profile described above are shown in FIGS. 9 and 12.

For example, as shown in FIG. 7, operation S21 of storing the driving record may be performed during an interval between particular events. For example, in operation S21, the control unit 13 may determine whether the end of the endoscope 910 is located at a particular site with respect to the protective sheath 11, based on a signal sensed through the sensor 14 (operation S211), and start storing the driving record from a corresponding point in time (operation S212). In addition, the control unit 13 may determine whether the surgical instrument 920 has performed a particular work based on the operation amount of the endoscope operating device 12 (operation S213), and end storing the driving record at a corresponding point in time (operation S214).

As another example, as shown in FIG. 8, operation S21' of storing the driving record may be performed during an interval between optional points in time that may be set based on an instruction from the operator. For example, in operation S21', the driving record may start to be stored depending on whether a driving record start instruction is input by the operator through the input unit 16 (operations S211' and S212), and storing the driving record may be ended depending on whether a driving record end instruction is input by the operator through the input unit 16 (operations S213' and S214).

If a stone is gripped in operation S16, the operator may operate the master device 15 to move the endoscope 910 backward together with the stone, or automatically operate the endoscope operating device 12 by transmitting, to the control unit 13 through the input unit 16, information indicating that the stone is gripped, thereby withdrawing the endoscope 910 from the protective sheath 11 in operation S17 and removing the stone by releasing the stone from the surgical instrument 920 in operation S18.

In operation S19, the control unit 13 may receive, from the operator, confirmation regarding whether the stone removal has been completed at the previous work position at which the basket job has been performed.

If information indicating that there is a stone remaining at the previous work position is input in operation S19, the control unit 13 may automatically cause the endoscope 910 to autonomous drive based on the existing driving record of the endoscope 910 collected in operation S21, thereby inserting the endoscope 910 again such that the end of the endoscope 910 is located at the same site of the previous work position, in operation S22. As such, operations S16 to S19 and S22 may be repeatedly performed until all the stones are withdrawn from the position at which the basket has gripped the stones. Through operation S22, the operator does not need to memorize the path that the endoscope 910 has passed to reach the previous work position and operate the master device 15 along the path. Since the operator only needs to perform the basket job (operation S16), the fatigue of surgery may be significantly reduced. In addition, since there is no trial and error that may occur until the operator finds the previous work position, the operation time may be significantly reduced.

When information indicating that the stone removal has been completed at the previous work position is input in operation S19, the control unit 13 may receive, from the operator, confirmation regarding whether the stone removal has been completed at all work positions, in operation S20.

When information indicating that there is a work position at which the stone removal is yet to be performed is input in operation S20, operation S12 may be performed, and sequentially operation S13 of scanning for stones may be performed.

Figure 9:
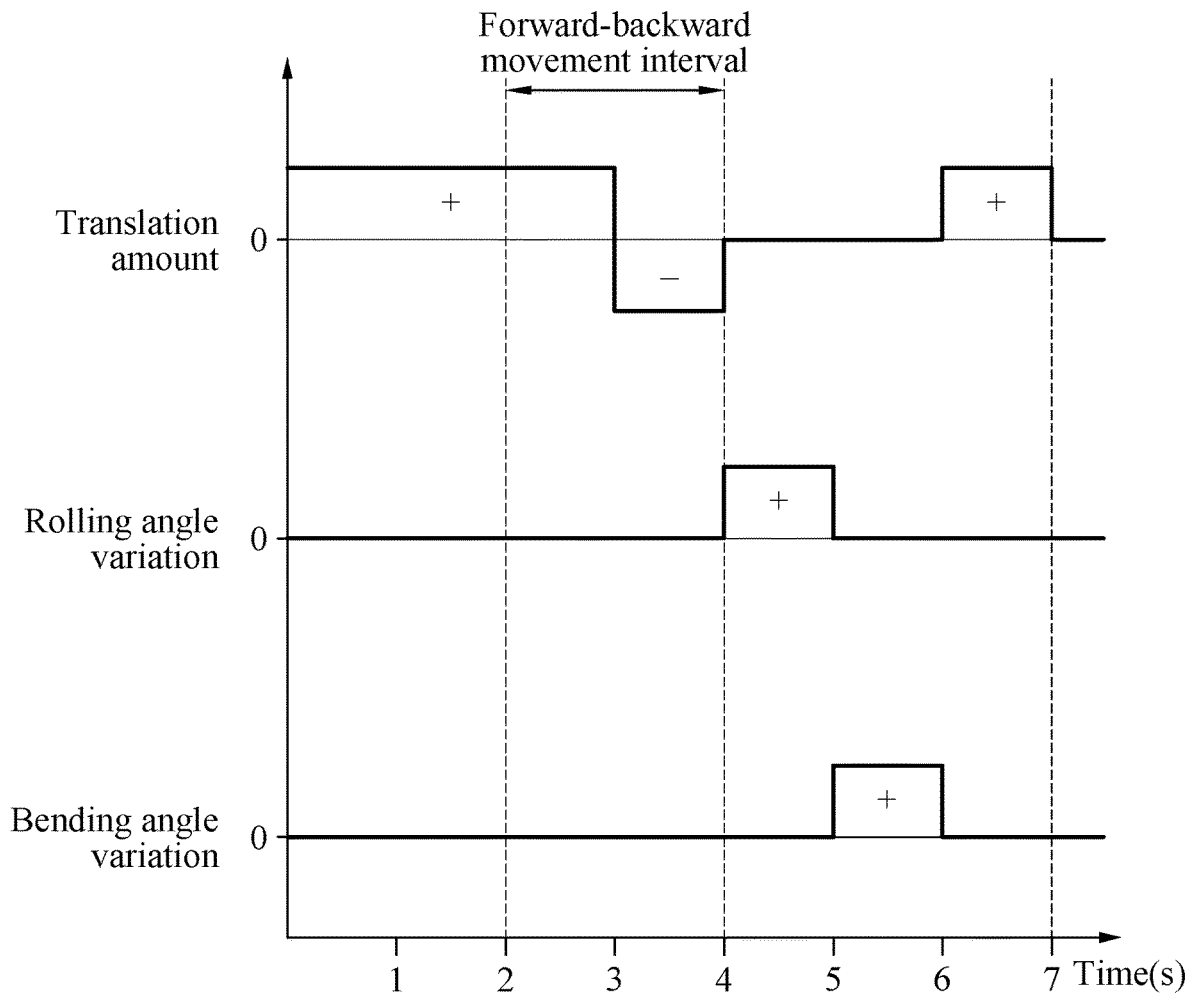
FIG. 9 illustrates an example of an operation profile represented as a graph showing over time an operation amount of an endoscope operating device operated by an operator during a particular interval.

FIG. 9 illustrates an example of an operation profile represented as a graph showing over time an operation amount of an endoscope operating device operated by an operator during a particular interval.

FIG. 9 shows a series of operations performed by an operator to move the endoscope 910 to a specific work position, wherein the operator moves the endoscope 910 forward in an incorrect direction, resulting in the end of the endoscope 910 to pass through a particular position (see the interval between 2 and 3 seconds), moves the endoscope 910 backward again (see the interval between 3 and 4 seconds), and then changes the direction that the end of the endoscope 910 faces (see the interval between 4 and 6 seconds), and moves the endoscope 910 forward (see the interval between 6 and 7 seconds).

Such a phenomenon may occur, for example, when the endoscope 910 is stuck in the inner wall of an organ of a patient and receives resistance. Nevertheless, if the endoscope 910 autonomously drives to the previous work position through repetition of the same operation using the operation profile without correction, repeated shocks are applied to the organ of the patient, which may cause a medical accident. In addition, the trial and error time for the forward and backward movements unnecessarily increases the operation time. Thus, embodiments for resolving this issue will be described below.

Figure 10:
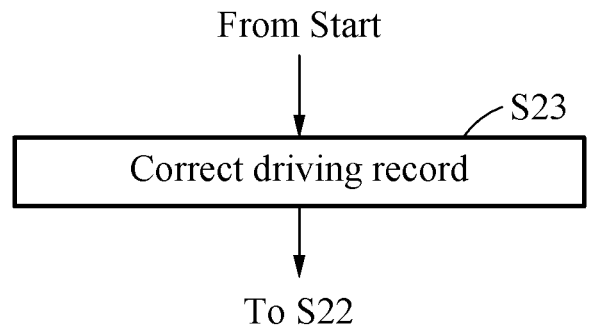
FIGS. 10 and 11 illustrate an operation of correcting a driving record according to an embodiment.
Figure 11:
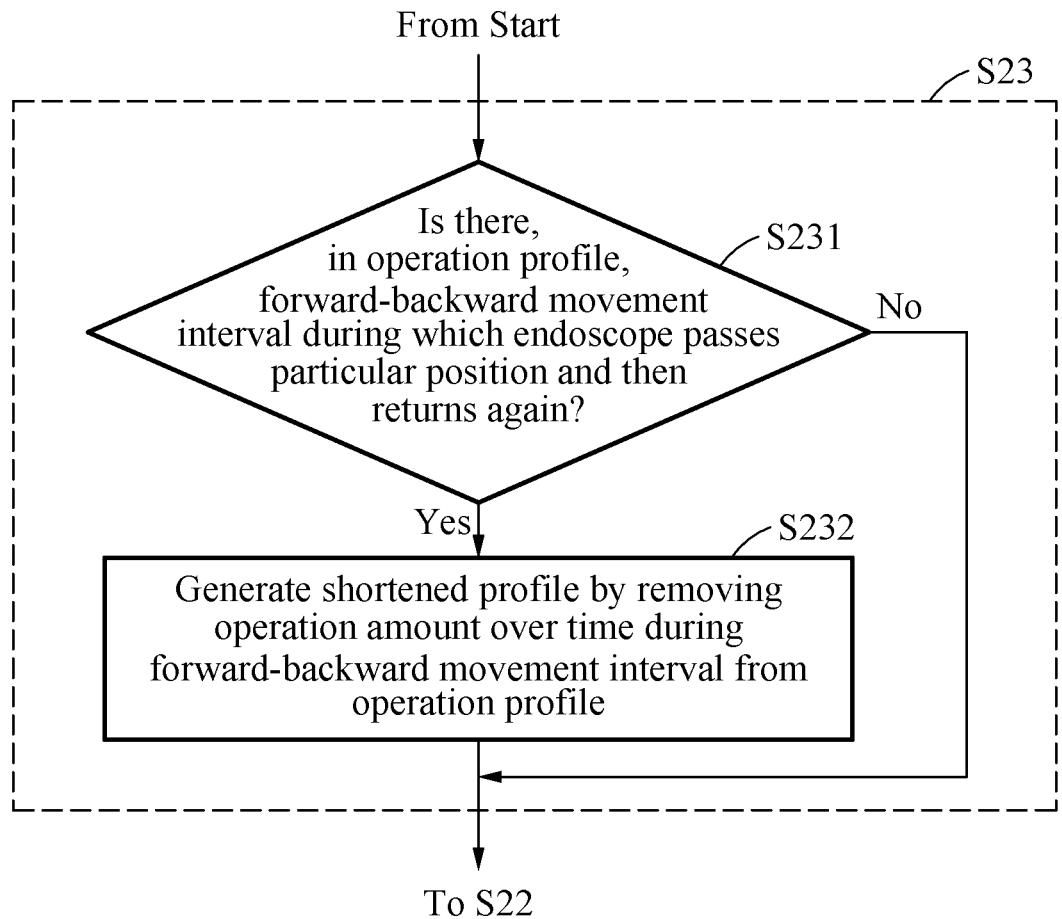

FIGS. 10 and 11 illustrate an operation of correcting a driving record according to an embodiment.

Referring to FIGS. 10 and 11, a control method for the autonomous endoscopic system 1 may further include operation S23 of correcting the driving record. Operation S23 includes operation S231 of determining whether there is a forward-backward movement interval and operation S232 of generating a shortened profile. Operation S22 may be performed using the shortened profile generated as above (see FIG. 6).

Here, the "forward-backward movement interval" refers to an interval, in the operation profile, during which the end of the endoscope 910 passes a particular position and returns again, and may be the interval between 2 and 4 seconds in FIG. 9.

If the control unit 13 determines that there is a forward-backward movement interval between a first point in time and a second point in time in operation S231, the control unit 13 may generate the shortened profile by removing the operation amount over time during the forward-backward movement interval (the interval between 2 and 4 seconds in FIG. 9) from the operation profile, in operation S232.

The control unit 13 may control the endoscope operating device 12 according to the shortened profile generated as above, thereby preventing a burden to the body of the patient. Further, if the operator finds a correct target site after several trials and errors, by omitting the trials and errors and enabling the endoscope 910 to move directly to the target site along the shortest path, the operation time may be significantly reduced.

Figure 12:
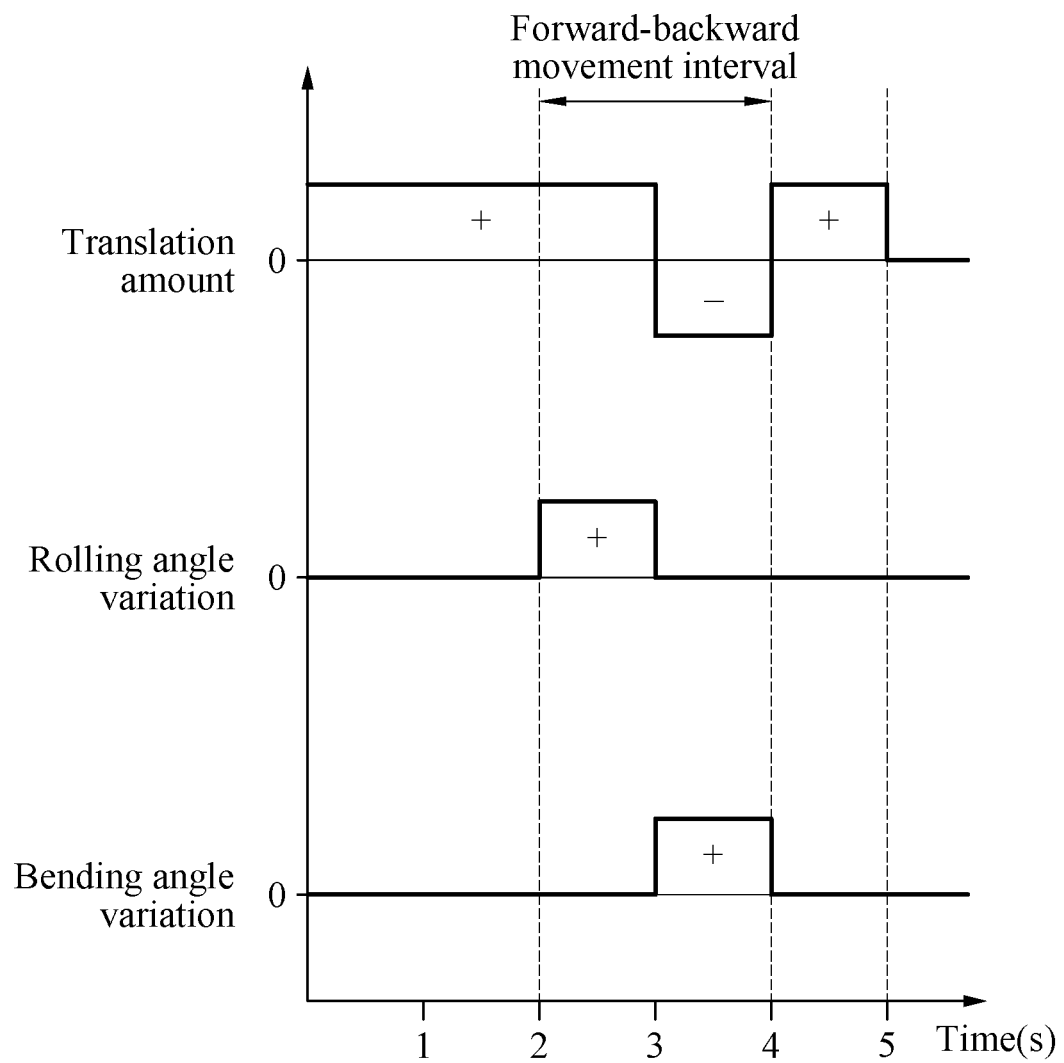
FIG. 12 illustrates another example of an operation profile represented as a graph showing over time an operation amount of an endoscope operating device operated by an operator during a particular interval.

FIG. 12 illustrates another example of an operation profile represented as a graph showing over time an operation amount of an endoscope operating device operated by an operator during a particular interval.

FIG. 12 shows a series of operations performed by an operator to move the endoscope 910 to a specific work position, wherein the operator moves the endoscope 910 forward in an incorrect direction, resulting in the end of the endoscope 910 to pass through a particular position (see the interval between 2 and 3 seconds), moves the endoscope 910 backward again (see the interval between 3 and 4 seconds), and then moves the endoscope 910 forward (see the interval between 4 and 5 seconds). The difference from the example of FIG. 9 is in that there are changes in a rolling angle and a bending angle. In this example, simply removing the forward-backward movement interval (the interval between 2 and 4 seconds) is not sufficient. Thus, an embodiment for resolving this issue will be described below.

Figure 13:
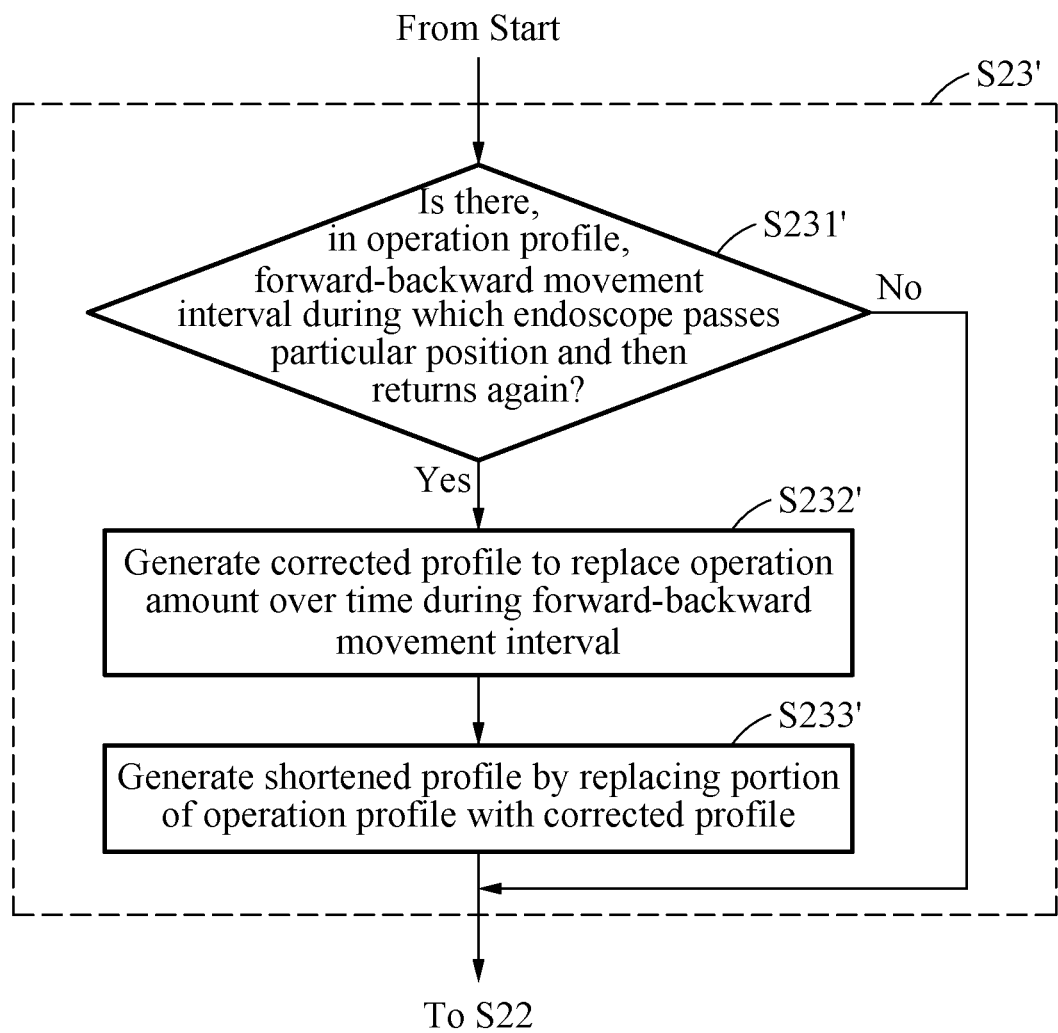
FIG. 13 illustrates an operation of correcting a driving record according to another embodiment.
Figure 14:
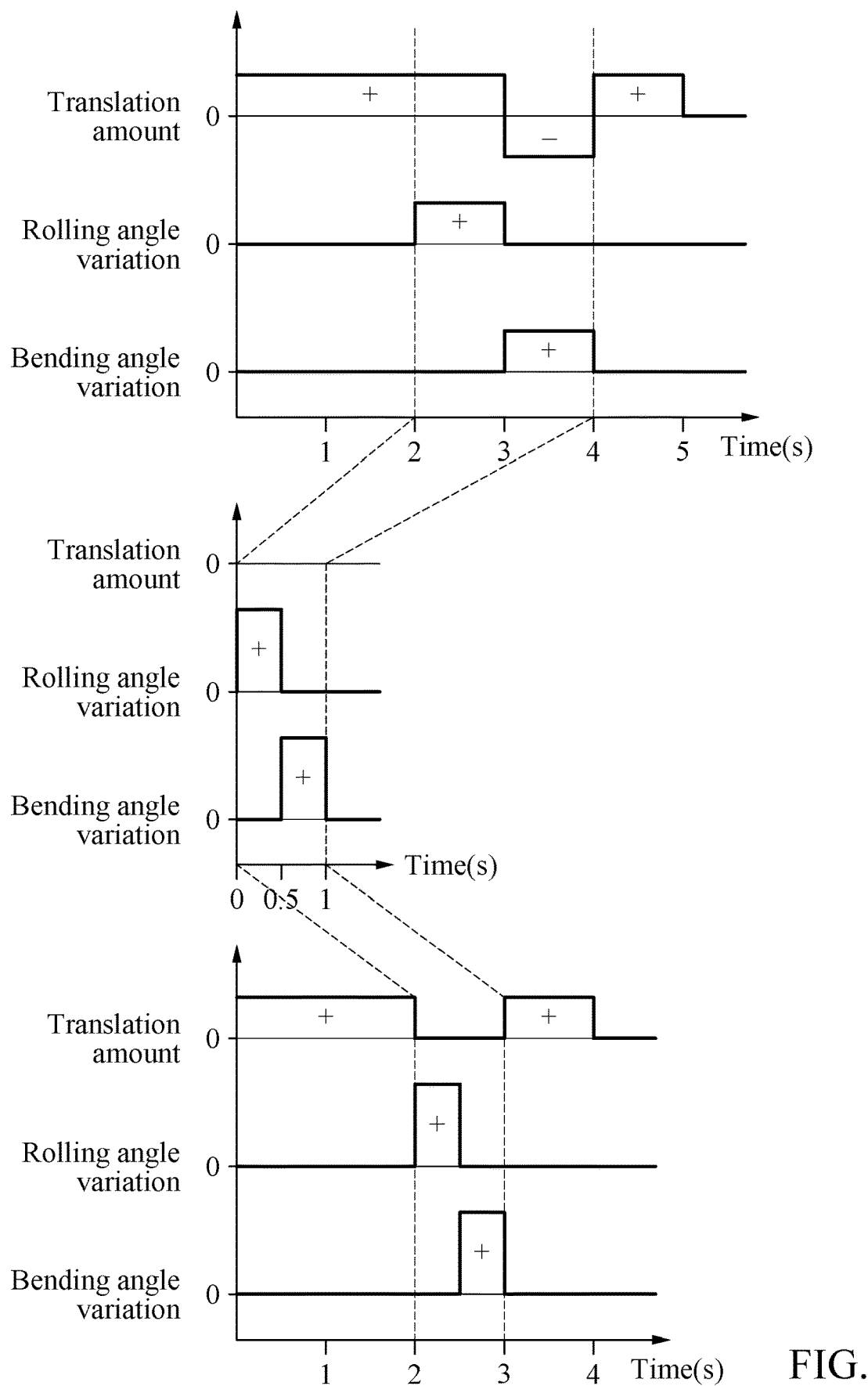
FIG. 14 illustrates a shortened profile generated by performing an operation of correcting a driving record according to another embodiment.

FIG. 13 illustrates an operation of correcting a driving record according to another embodiment, and FIG. 14 illustrates a shortened profile generated by performing the operation of correcting a driving record according to another embodiment.

Referring to FIGS. 13 and 14, operation S23' of correcting the driving record includes operation S231' of determining whether there is a forward-backward movement interval, operation S232' of generating a corrected profile, and operation S233' of generating a shortened profile. Operation S22 may be performed using the shortened profile generated as above (see FIG. 6).

In operation S232', the "corrected profile" may be, for example, an operation amount over time that includes a rolling angle variation and a bending angle variation during the forward-backward movement interval and that does not include a translation amount during the forward-backward movement interval.

In operation S233', the control unit 13 may generate the shortened profile by replacing the operation amount over time during the forward-backward movement interval in the operation profile with the corrected profile.

By this method, even if the moving direction of the end of the endoscope 910 changes during the forward-backward movement interval, the change may be reflected in the driving record of the endoscope 910, and unnecessary repetition of forward and backward translations during the autonomous driving of the endoscope 910 may be prevented. In addition, as shown in FIG. 14, the corrected profile may be performed at a higher rate of change for a time shorter than the forward-backward movement interval, thereby further shortening the operation time.

A number of embodiments have been described above. Nevertheless, it should be understood that various modifications may be made to these embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

The invention claimed is:

1. An autonomous endoscopic system capable of controlling movement of an endoscope inserted into a protective sheath installed in a body of a patient, the autonomous endoscopic system comprising:
    an endoscope operating device capable of adjusting a relative position of the endoscope with respect to the protective sheath, a rolling angle of the endoscope, and a bending angle of a bending portion which is located at an end of the endoscope and is bendable; and
    a controller for controlling the endoscope operating device,
    a display for outputting an image of an inside of the body of the patient to an operator,
    a clutch operable by the operator and capable of allowing or stopping a continuous drive of the endoscope operating device,
    a master device located at a site spaced apart from the endoscope operating device and configured to be operated by the operator to remotely operate the endoscope operating device,
    wherein the controller is configured to control the endoscope operating device on the basis of a driving record of the endoscope,
    wherein a basket for gripping a stone present inside the body of the patient is configured to be inserted into the endoscope, and
    the controller is configured to control the endoscope operating device such that the endoscope automatically returns to the site where the endoscope was located at a point in time the basket completes a gripping operation.

2. The autonomous endoscopic system of claim 1, wherein the protective sheath is configured to maintain a fixed position inside the body of the patient irrespective of the movement of the endoscope, the protective sheath and the endoscope operating device are fixed to each other through a fixing tool, and
    wherein the controller is configured to drive the endoscope by detecting a relative position between the protective sheath and the endoscope from the image.

3. The autonomous endoscopic system of claim 1, wherein the controller is configured to control the display to display the image by overlaying, on the image, an expected position and pose of the endoscope at a point in time after a set time elapses from a current time.

4. The autonomous endoscopic system of claim 3, wherein the controller is configured to determine, while the image is in the overlapped state, whether to continue allowing an autonomous driving of the endoscope without an additional operation or stop the autonomous driving and directly drive the endoscope using the master device.

5. The autonomous endoscopic system of claim 1, wherein a basket for gripping a stone present inside the body of the patient is configured to be inserted into the endoscope, and when the basket completes a gripping operation, the controller is configured to control the endoscope operating device (a) to withdraw the endoscope from the protective sheath, (b) to release the gripped stone by opening the basket, and (c) to cause the endoscope to re-enter, such that the endoscope automatically returns to the site where the endoscope was located at a point in time the basket completes the gripping operation.

6. The autonomous endoscopic system of claim 1, wherein the driving record includes an operation profile that shows an operation amount of the endoscope operating device over time from a first point in time to a second point in time.

7. The autonomous endoscopic system of claim 6, wherein the first point in time is a point in time the end of the endoscope is located at a particular site with respect to the protective sheath.

8. The autonomous endoscopic system of claim 6, wherein the second point in time is a point in time at which a surgical instrument inserted into the endoscope performs a particular work.

9. The autonomous endoscopic system of claim 6, wherein at least one of the first point in time and the second point in time is an optional point in time to be set by the operator.

10. The autonomous endoscopic system of claim 6, wherein the operation amount includes a translation amount of the endoscope, a rolling angle variation of the endoscope, and a bending angle variation of the endoscope.

11. The autonomous endoscopic system of claim 10, wherein the controller:
    (a) determines whether there is, between the first point in time and the second point in time, a forward-backward movement interval during which the endoscope passes a particular position and then returns again,
    (b) generates, if there is the forward-backward movement interval, a shortened profile by removing the operation amount over time during the forward-backward movement interval from the operation profile, and
    (c) controls the endoscope operating device according to the shortened profile.

12. The autonomous endoscopic system of claim 10, wherein the controller is configured to:
    (a) determine whether there is, between the first point in time and the second point in time, a forward-backward movement interval during which the endoscope passes a particular position and then returns again,
    (b) generate, if there is the forward-backward movement interval, a corrected profile that includes a rolling angle variation and a bending angle variation during the forward-backward movement interval, that does not include the translation amount during the forward-backward movement interval, and that is performed for a time shorter than the forward-backward movement interval,
    (c) generate a shortened profile by replacing the operation amount over time during the forward-backward movement interval in the operation profile with the corrected profile, and
    (d) control the endoscope operating device according to the shortened profile.

13. The autonomous endoscopic system of claim 1, wherein the controller initializes a pose of the endoscope such that the endoscope has a particular rolling angle and a particular bending angle when the end of the endoscope is located at a particular site with respect to the protective sheath.

\* \* \* \* \*